United States Patent [19]

Elbe et al.

[11] Patent Number: 4,879,385
[45] Date of Patent: Nov. 7, 1989

[54] SUBSTITUTED HYDROXYALKYL-AZOLES AND THEIR USE AS ANTIMYCOTICS

[75] Inventors: Hans-Ludwig Elbe, Wuppertal; Karl H. Büchel, Burscheid; Klaus Schaller; Manfred Plempel, both of Wuppertal, all of Fed. Rep. of Germany

[73] Assignee: Bayer Aktiengesellschaft, Leverkusen, Fed. Rep. of Germany

[21] Appl. No.: 62,251

[22] Filed: Jun. 15, 1987

Related U.S. Application Data

[63] Continuation of Ser. No. 663,285, Oct. 22, 1984, abandoned, which is a continuation of Ser. No. 476,096, Mar. 17, 1983, abandoned.

[30] Foreign Application Priority Data

Apr. 2, 1982 [DE] Fed. Rep. of Germany ....... 3212388

[51] Int. Cl.$^4$ .................. A61K 31/41; A61K 31/415; C07D 249/12; C07D 233/60
[52] U.S. Cl. .................................... 514/383; 514/399; 548/262; 548/341
[58] Field of Search ................. 514/383, 399; 548/262

[56] References Cited

U.S. PATENT DOCUMENTS

| | | | |
|---|---|---|---|
| 4,414,210 | 11/1983 | Miller et al. | 548/101 |
| 4,507,140 | 3/1985 | Sugavanam | 548/262 |
| 4,549,900 | 10/1985 | Kramer et al. | 548/262 |
| 4,734,126 | 3/1988 | Holmwood et al. | 548/262 |

FOREIGN PATENT DOCUMENTS

| | | | |
|---|---|---|---|
| 061835 | 6/1982 | European Pat. Off. | 548/262 |
| 3018865 | 11/1981 | Fed. Rep. of Germany | 514/383 |
| 2103210 | 2/1983 | United Kingdom | 548/262 |

*Primary Examiner*—Richard L. Raymond
*Assistant Examiner*—Patricia L. Morris
*Attorney, Agent, or Firm*—Sprung Horn Kramer & Woods

[57] ABSTRACT

The invention relates to substituted hydroxyalkylazoles defined herein by formula (I), which compounds are useful as antimycotic agents. Also included in the invention are compositions containing said compounds and methods for the use of said compounds and compositions. In addition, the invention includes methods for the manufacture of the compounds of formula (I).

14 Claims, No Drawings

SUBSTITUTED HYDROXYALKYL-AZOLES AND THEIR USE AS ANTIMYCOTICS

This is a continuation of application Ser. No. 663,285, filed Oct. 22, 1984 now abandoned which is a continuation of Ser. No. 476,096, filed Mar. 17, 1983 now abandoned.

The present invention relates to new substituted hydroxyalkyl-azoles, a process for their preparation and their use as antimycotics.

It has already been disclosed that certain hydroxyalkylazolyl derivatives, such as, for example, 1,2-bis(4-chlorophenyl)-2-hydroxy-3-(imidazol-1-yl)-propane or 1,1-bis(3-chlorophenyl)-1-hydroxy-2-(imidazol-1-yl)-ethane and 2-(4-biphenyl)-2 hydroxy-1-phenyl-3-(1,2,4-triazol-1-yl)-propane, have good antimycotic properties [compare DE-OS 2,623,129 corresponding to U.S. Ser. No. 290,805 and DE-OS 2,851,086 corresponding to U.S. Pat. No. 4,381,306]. the action of these compounds is not always completely satisfactory, in particular when low concentrations are used.

New substituted hydroxyalkyl-azoles of the general formula

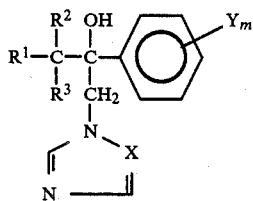

(I)

in which

R$^1$ represents phenyl, —O-phenyl, —S-phenyl, —SO-phenyl, —SO$_2$-phenyl, —CH$_2$-phenyl, —CH$_2$—O-phenyl, —CH$_2$—S-phenyl —CH$_2$—SO-phenyl or —CH$_2$—SO$_2$-phenyl, each of which is optionally substituted, R$^2$ represents alkyl, especially alkyl having 1 to 8, particularly 1 to 4 carbon atoms, R$^3$ represents alkyl, especially alkyl having 1 to 8, particularly 1 to 4 carbon atoms, X represents a nitrogen atom or the CH group, Y represents halogen (more particularly fluorine, chlorine or bromine), alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenylalkoxy, and m represents the numbers 0, 1, 2 or 3, and their acid addition salts have been found.

The compounds of the formula (I) possess an asymmetric carbon atoms, and can therefore occur in the forms of two optical isomers.

Racemate mixtures can be separated into the pure racemates in a known manner on the basis of the physicochemical differences of the constituents, for example by chromatography and/or fractional crystallization.

Pure racemates can be resolved according to known methods, for example by recrystallization from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

Furthermore, it has been found that the substituted hydroxyalkyl-azoles of the formula (I) are obtained when oxiranes of the formula

(II)

in which

R$^1$, R$^2$, R$^3$ Y and m have the meaning given above, are reacted with azoles of the formula

(III)

in which

X has the meaning given above and

M represents hydrogen or analkali metal, in the presence of a diluent and, if appropriate, in the presence of a base, and, if appropriate, the resulting hydroxyalkyl-azoles of the formula

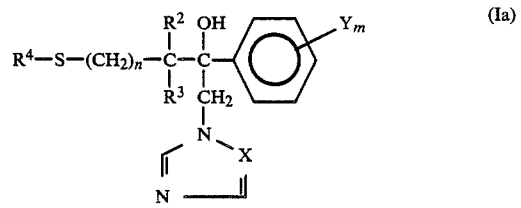

(Ia)

in which

R$^2$, R$^3$, X, Y and m have the meaning given above,

R$^4$ represents optionally substituted phenyl, and n represents the numbers 0 or 1, are oxidised in a customary manner, according to known methods.

If desired, adducts of the resulting compounds of the formula (I) with an acid can then be formed.

The new substituted hydroxyalkyl-azoles of the formula (I) have powerful antimycotic properties. In this respect, the compounds according to the invention surprisingly exhibit, in particular, a better therapeutically useful in vivo activity than the compounds 1,2-bis(4-chlorophenyl)-2-hydroxy-3-(imidazol-1-yl)-propane or 1,1-bis(3-chlorophenyl)-1-hydroxy-2-(imidazol-1-yl)-ethane and 2-(4-bisphenylyl)-2-hydroxy-1-phenyl-3-(1,2,4-triazol-1-yl)-propane, which are known from the prior art and are similar compounds chemically. The substances according to the invention thus represent an enrichment of medicine.

In addition, the new substituted hydroxylalkylazoles are interesting intermediate products. Thus, for example, the compounds of the formula (I) can be converted in a customary manner at the hydroxyl group to give the corresponding ethers. Furthermore, acyl or carbamoyl derivatives of the compounds of the formula (I) can be obtained by reaction with, for example acyl halides or carbamoyl chlorides, in a manner which is known in principle Formula (I) gives a general definition of the substituted hydroxyalkylazoles according to the invention. In this formula $R^1$ preferably represents phenyl, —O-phenyl —S-phenyl, —SO-phenyl, —SO$_2$-phenyl, —CH$_2$-phenyl, —CH$_2$—O-phenyl, —CH$_2$—S-phenyl, —CH$_2$—SO-phenyl or —CH$_2$—SO$_2$-phenyl, each of which is monosubstituted to disubstituted by identical or different substituents, the phenyl substituents which may be mentioned preferably having the meanings of Y;

$R^2$ preferably represents straight-chain or branched alkyl having 1 to 4 carbon atoms;

$R^3$ preferably represents straight-chain or branched alkyl having 1 to 4 carbon atoms;

X preferably represents a nitrogen atom or the CH group;

Y preferably represents halogen (especially fluorine or chlorine); alkyl having 1 to 4 carbon atoms; cycloalkyl having 5-7 carbon atoms; alkoxy and alkylthio, each having 1 to 4 carbon atoms, halogenoalkyl, halogenoalkoxy and halogenoalkylthio, each having 1 to 2 carbon atoms and 1 to 5 identical or different halogen atoms, such as, preferably fluorine atoms and chlorine atoms; and preferably represents phenyl, phenoxy, phenylalkyl and phenylalkoxy which have 1 to 2 carbon atoms in the alkyl part or in the alkoxy part, and each of which are optionally substituted (especially mono- or di-substituted by halogen or alkyl having 1 to 2 carbon atoms, and m preferably represents one of the numbers 0, 1 2 or 3

Particularly preferred compounds of the formula (I) are those in which $R^1$ represents phenyl, —O-phenyl, —S-phenyl, —SO-phenyl, —SO$_2$-phenyl, —CH$_2$-phenyl, —CH$_2$—O-phenyl, —CH$_2$—S-phenyl, —CH$_2$—SO-phenyl or —CH$_2$—SO$_2$-phenyl, each of which is monosubstituted to disubstituted by identical or different substituents, the phenyl substituents which may be mentioned preferably having the meanings of Y;

$R^2$ represents methyl or ethyl, $R^3$ represents methyl or ethyl,

X represents a nitrogen atom or the CH group,

Y represents fluorine, chlorine, bromine, methyl, isopropyl tert.-butyl, cyclohexyl, methoxy, methylthio, trifluoromethyl, trifluoromethoxy and trifluoromethylthio, and represents phenoxy, benzyl, benzyloxy or phenyl which is optionally substituted by fluorine, chlorine or methyl, and m represents the numbers 0, 1 or 2.

Preferred compounds according to the invention are also addition products of acids and those substituted hydroxyalkyl-azoles, of the formula (I) in which the substituents $R^1$, $R^2$, $R^3$, X and $Y_m$ have the meanings which have already been mentioned as being preferred for these substituents.

The acids which can be used to form adducts preferably include hydrohalic acids, such as, for example, hydrochloric acid and hydrobromic acid, in particular hydrochloric acid, and also phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids such as p-toluenesulphonic acid and naphthalene-1,5-disulphonic acid.

In addition to the compounds mentioned in the preparation examples, the following compounds of the formula (I), prepared in a manner analogous to that shown in the preparation examples, may be mentioned individually (X represents both a nitrogen atom and the CH group):

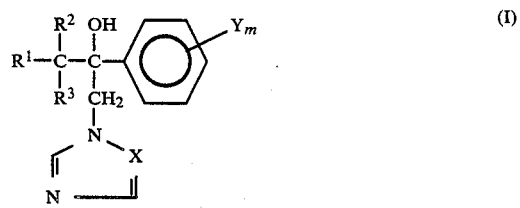

(I)

| $R^1$ | $R^2$ | $R^3$ | $Y_m$ |
|---|---|---|---|
| F—⟨phenyl⟩—O— | CH$_3$ | CH$_3$ | 2-Cl |
| ⟨2-F-phenyl⟩—O— | CH$_3$ | CH$_3$ | 2-Cl |
| Cl—⟨phenyl⟩—O— | CH$_3$ | CH$_3$ | 3-Cl |
| ⟨2-Cl-phenyl⟩—O— | CH$_3$ | CH$_3$ | 3,4-Cl$_2$ |
| ⟨2-Cl-phenyl⟩—O— | CH$_3$ | CH$_3$ | 3-Cl |
| Cl—⟨2-Cl-phenyl⟩—O— | CH$_3$ | CH$_3$ | 3-Cl |
| Cl—⟨phenyl⟩—O— | CH$_3$ | CH$_3$ | 2,4-Cl$_2$ |
| F—⟨phenyl⟩—O— | CH$_3$ | CH$_3$ | 2,4-Cl$_2$ |

| R¹ | R² | R³ | Y_m |
|---|---|---|---|
| 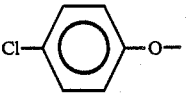 | CH₃ | CH₃ | 3,4-Cl₂ |
| 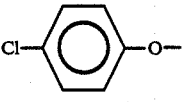 | CH₃ | CH₃ | 2-CH₃, 4-Cl |
| 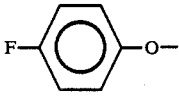 | CH₃ | CH₃ | 3,4-Cl₂ |
| 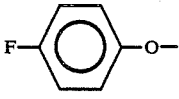 | CH₃ | CH₃ | 2-CH₃, 4-Cl |
| 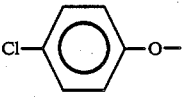 | CH₃ | CH₃ | 2-Cl |
| 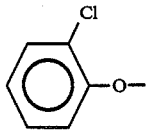 | CH₃ | CH₃ | 2-Cl |
| 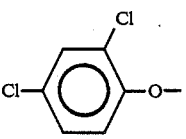 | CH₃ | CH₃ | 4-Cl |
| 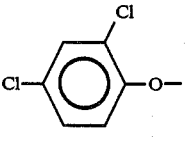 | CH₃ | CH₃ | 2,4-Cl₂ |
| 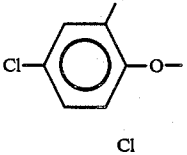 | CH₃ | CH₃ | 2-Cl |
| 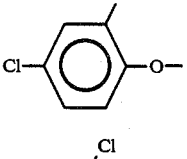 | CH₃ | CH₃ | 4-F |
| 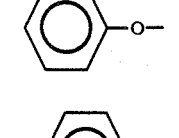 | CH₃ | CH₃ | 4-F |
|  | CH₃ | CH₃ | 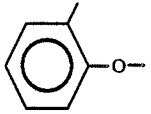 |
| 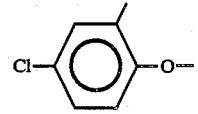 | CH₃ | CH₃ |  |
| 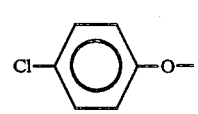 | CH₃ | CH₃ | 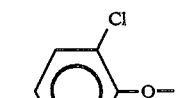 |
|  | CH₃ | CH₃ | 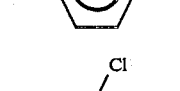 |
| 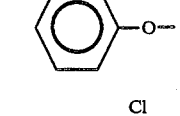 | CH₃ | CH₃ | 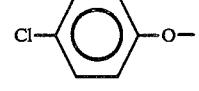 |
| 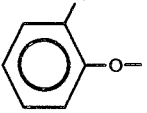 | CH₃ | CH₃ | 4-Cl |
| 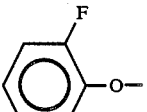 | CH₃ | CH₃ | 2-F |
| 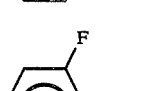 | CH₃ | CH₃ | 2-F |
| (Cl,Cl-phenyl)-O— | CH₃ | CH₃ | 2-F |
| (Cl-phenyl)-O— | CH₃ | CH₃ | 2,4-Cl₂ |
| (F-phenyl)-O— | CH₃ | CH₃ | 2,4-Cl₂ |
| (F-phenyl)-O— | CH₃ | CH₃ | 4-Cl |
| (F-phenyl)-S— | CH₃ | CH₃ | 2-Cl |

-continued

| R¹ | R² | R³ | Yₘ |
|---|---|---|---|
| 2-F-C₆H₄-S— | CH₃ | CH₃ | 2-Cl |
| 4-Cl-C₆H₄-S— | CH₃ | CH₃ | 3-Cl |
| 2-Cl-C₆H₄-S— | CH₃ | CH₃ | 3,4-Cl₂ |
| 2-Cl-C₆H₄-S— | CH₃ | CH₃ | 3-Cl |
| 2,4-Cl₂-C₆H₃-S— | CH₃ | CH₃ | 3-Cl |
| 4-Cl-C₆H₄-S— | CH₃ | CH₃ | 2,4-Cl₂ |
| 4-F-C₆H₄-S— | CH₃ | CH₃ | 2,4-Cl₂ |
| 4-Cl-C₆H₄-S— | CH₃ | CH₃ | 3,4-Cl₂ |
| 4-Cl-C₆H₄-S— | CH₃ | CH₃ | 2-CH₃, 4-Cl |
| 4-F-C₆H₄-S— | CH₃ | CH₃ | 3,4-Cl₂ |
| 4-F-C₆H₄-S— | CH₃ | CH₃ | 2-CH₃, 4-Cl |
| 4-Cl-C₆H₄-S— | CH₃ | CH₃ | 2-Cl |

-continued

| R¹ | R² | R³ | Yₘ |
|---|---|---|---|
| 2-Cl-C₆H₄-S— | CH₃ | CH₃ | 2-Cl |
| 2,4-Cl₂-C₆H₃-S— | CH₃ | CH₃ | 4-Cl |
| 2,4-Cl₂-C₆H₃-S— | CH₃ | CH₃ | 2,4-Cl₂ |
| 2,4-Cl₂-C₆H₃-S— | CH₃ | CH₃ | 2-Cl |
| 2,4-Cl₂-C₆H₃-S— | CH₃ | CH₃ | 4-F |
| 2-Cl-C₆H₄-S— | CH₃ | CH₃ | 4-F |
| 4-Cl-C₆H₄-S— | CH₃ | CH₃ | 4-(4-Cl-C₆H₄) |
| 2-Cl-C₆H₄-S— | CH₃ | CH₃ | 4-(4-Cl-C₆H₄) |
| 2,4-Cl₂-C₆H₃-S— | CH₃ | CH₃ | 4-(4-Cl-C₆H₄) |
| 4-F-C₆H₄-S— | CH₃ | CH₃ | 4-(4-Cl-C₆H₄) |
| 4-Cl-C₆H₄-S— | CH₃ | CH₃ | 4-O-(4-Cl-C₆H₄) |

| R¹ | R² | R³ | Yₘ |
|---|---|---|---|
| 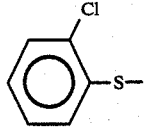 | CH₃ | CH₃ | 4-Cl |
| 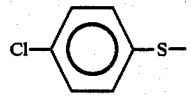 | CH₃ | CH₃ | 2-F |
| 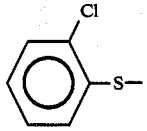 | CH₃ | CH₃ | 2-F |
| 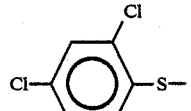 | CH₃ | CH₃ | 2-F |
| 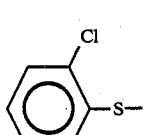 | CH₃ | CH₃ | 2,4-Cl₂ |
| 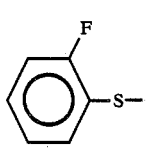 | CH₃ | CH₃ | 2,4-Cl₂ |
| 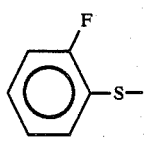 | CH₃ | CH₃ | 4-Cl |
| 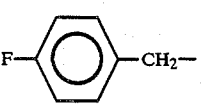 | CH₃ | CH₃ | 2-Cl |
| 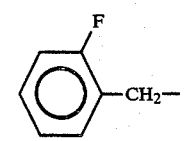 | CH₃ | CH₃ | 2-Cl |
| 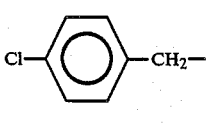 | CH₃ | CH₃ | 3-Cl |
| 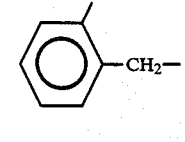 | CH₃ | CH₃ | 3,4-Cl₂ |
| 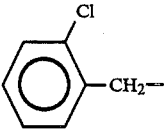 | CH₃ | CH₃ | 3-Cl |
| 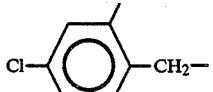 | CH₃ | CH₃ | 3-Cl |
| 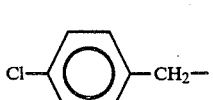 | CH₃ | CH₃ | 2,4-Cl₂ |
| 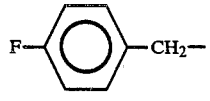 | CH₃ | CH₃ | 2,4-Cl₂ |
| 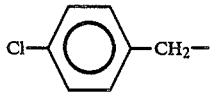 | CH₃ | CH₃ | 3,4-Cl₂ |
| 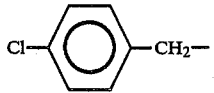 | CH₃ | CH₃ | 2-CH₃, 4-Cl |
| 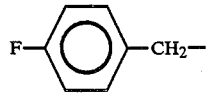 | CH₃ | CH₃ | 3,4-Cl₂ |
| 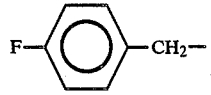 | CH₃ | CH₃ | 2-CH₃, 4-Cl |
| 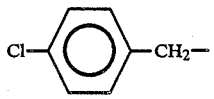 | CH₃ | CH₃ | 2-Cl |
| 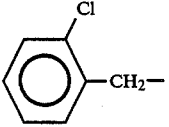 | CH₃ | CH₃ | 2-Cl |
| 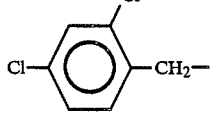 | CH₃ | CH₃ | 4-Cl |
| 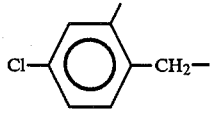 | CH₃ | CH₃ | 2,4-Cl₂ |

-continued

| R¹ | R² | R³ | Yₘ |
|---|---|---|---|
| 2,4-diClC₆H₃CH₂− | CH₃ | CH₃ | 2-Cl |
| 2,4-diClC₆H₃CH₂− | CH₃ | CH₃ | 4-F |
| 2-ClC₆H₄CH₂− | CH₃ | CH₃ | 4-F |
| 4-ClC₆H₄CH₂− | CH₃ | CH₃ | 4-ClC₆H₄− |
| 2-ClC₆H₄CH₂− | CH₃ | CH₃ | 4-ClC₆H₄− |
| 2,4-diClC₆H₃CH₂− | CH₃ | CH₃ | 4-ClC₆H₄− |
| 4-FC₆H₄CH₂− | CH₃ | CH₃ | 4-ClC₆H₄− |
| 4-ClC₆H₄CH₂− | CH₃ | CH₃ | 4-O-C₆H₄-Cl |
| 2-ClC₆H₄CH₂− | CH₃ | CH₃ | 4-Cl |
| 4-ClC₆H₄CH₂− | CH₃ | CH₃ | 2-F |
| 2-ClC₆H₄CH₂− | CH₃ | CH₃ | 2-F |
| 2,4-diClC₆H₃CH₂− | CH₃ | CH₃ | 2-F |
| 2-ClC₆H₄CH₂− | CH₃ | CH₃ | 2,4-Cl₂ |
| 2-FC₆H₄CH₂− | CH₃ | CH₃ | 2,4-Cl₂ |
| 2-FC₆H₄CH₂− | CH₃ | CH₃ | 4-Cl |
| 4-FC₆H₄− | CH₃ | CH₃ | 2-Cl |
| 2-FC₆H₄− | CH₃ | CH₃ | 2-Cl |
| 4-ClC₆H₄− | CH₃ | CH₃ | 3-Cl |
| 2,4-diClC₆H₃− | CH₃ | CH₃ | 3,4-Cl₂ |
| 2-ClC₆H₄− | CH₃ | CH₃ | 3-Cl |
| 4-ClC₆H₄− | CH₃ | CH₃ | 3-Cl |
| 4-ClC₆H₄− | CH₃ | CH₃ | 2,4-Cl₂ |
| 4-FC₆H₄− | CH₃ | CH₃ | 2,4-Cl₂ |
| 4-ClC₆H₄− | CH₃ | CH₃ | 3,4-Cl₂ |

-continued

| R¹ | R² | R³ | Yₘ |
|---|---|---|---|
| 4-Cl-phenyl | CH₃ | CH₃ | 2-CH₃, 4-Cl |
| 4-F-phenyl | CH₃ | CH₃ | 3,4-Cl₂ |
| 4-F-phenyl | CH₃ | CH₃ | 2-CH₃, 4-Cl |
| 4-Cl-phenyl | CH₃ | CH₃ | 2-Cl |
| 2-Cl-phenyl | CH₃ | CH₃ | 2-Cl |
| 2,4-Cl₂-phenyl | CH₃ | CH₃ | 4-Cl |
| 2,4-Cl₂-phenyl | CH₃ | CH₃ | 2,4-Cl₂ |
| 2,4-Cl₂-phenyl | CH₃ | CH₃ | 2-Cl |
| 2,4-Cl₂-phenyl | CH₃ | CH₃ | 4-F |
| 2-Cl-phenyl | CH₃ | CH₃ | 4-F |
| 2,4-Cl₂-phenyl | CH₃ | CH₃ | 4-(4-Cl-phenyl) |
| 2-Cl-phenyl | CH₃ | CH₃ | 4-(4-Cl-phenyl) |
| 2,4-Cl₂-phenyl | CH₃ | CH₃ | 4-(4-Cl-phenyl) |
| 2-F-phenyl | CH₃ | CH₃ | 4-(4-Cl-phenyl) |
| 2,4-Cl₂-phenyl | CH₃ | CH₃ | 4-O-(4-Cl-phenyl) |
| 2-Cl-phenyl | CH₃ | CH₃ | 4-Cl |
| 4-Cl-phenyl | CH₃ | CH₃ | 2-F |
| 2-Cl-phenyl | CH₃ | CH₃ | 2-F |
| 2,4-Cl₂-phenyl | CH₃ | CH₃ | 2-F |
| 2-Cl-phenyl | CH₃ | CH₃ | 2,4-Cl₂ |
| 2-F-phenyl | CH₃ | CH₃ | 2,4-Cl₂ |
| 2-F-phenyl | CH₃ | CH₃ | 4-Cl |

If, for example, 2-(4-chlorophenyl)-2-(4-chlorophenyl-tert.-butyl)-oxirane and 1,2,4-triazole are used as starting materials, the course of the process according to the invention can be represented by the following equation:

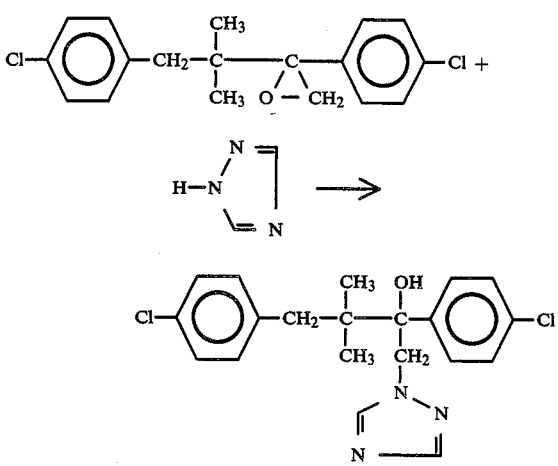

If for example 2-(4-chlorophenyl)-4-(4-chlorophenyl-thio)-3,3-dimethyl-1-(imidazol-1-yl)-2-butanol and hydrogen peroxide in glacial acetic acid are used as starting materials, the course of the oxidation according to the invention can be represented by the following equation:

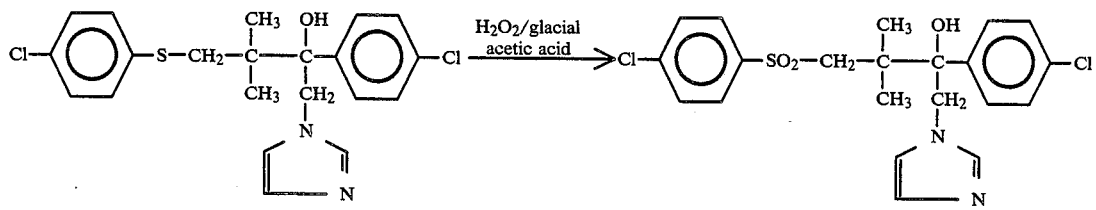

Formula (II) gives a general definition of the oxiranes to be used as starting materials for carrying out the process according to the invention. In this formula, $R^1$, $R^2$, $R^3$, Y and the index m preferably have the meanings which have already been mentioned in connection with the description of the substances according to the invention, of the formula (I) as being preferred for these substituents or for the index m.

The oxiranes of the formula (II) are not yet known. However, they can be obtained in a generally known manner by reacting a ketone of the formula

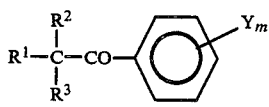 (IV)

in which $R^1$, $R^2$, $R^3$, Y and m have the meaning given above, either ($\alpha$) with dimethyloxosulphonium methylide of the formula

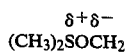 (V)

in the presence of a diluent, or ($\beta$) with trimethylsulphonium methyl-sulphate of the formula

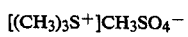 (VI)

in the presence of an inert organic solvent and in the presence of a base.

Some of the ketones of the formula (IV) which are required as starting materials in the preparation of the oxiranes of the formula (II) are known [compare, for example, J. Am. Chem. Soc. 1981, pages 4200 et seq. Zh. Org. Khim. p (1973), 544–46, Bull. Soc. Chem. France 1972, 7, 2756–59 and Zh Org. Khim. 12 (1976) 967–69]; or they can be prepared by processes which are known in principle.

Dimethyloxosulphonium methylide of the formula (V), which is required in process variant ($\alpha$), is known [compare J. Am. Chem. Soc 87 1363–1364 (1965)]. In the above reaction, it is employed in the freshly prepared state by producing it in situ by reaction of trimethyloxosulphonium iodide with sodium hydride or sodium amide in the presence of a diluent.

Trimethylsulphonium methyl-sulphate of the formula (VI), which is required in process variant ($\beta$), is likewise known [compare Heterocycles 8, 397 (1977)]. In the above reaction, it is likewise employed in the freshly prepared state by producing it in situ by reaction of dimethyl sulphide with dimethyl sulphate.

In variant ($\alpha$) of the process for the preparation of the oxiranes of the formula (II), dimethylsulphoxide is the preferred diluent.

In the process variant ($\alpha$) described above, the reaction temperatures can be varied within a relatively wide range. In general the reaction is carried out at temperatures between 20° C. and 80° C.

The process for the preparation of the oxiranes of the formula (II) in accordance with variant ($\alpha$), and the working-up of the reaction mixture obtained in this synthesis, are carried out according to customary methods [compare J. Am. Chem. Soc. 87 1363–1364 (1965)].

In variant ($\beta$) for the preparation of the oxiranes of the formula (II), the inert organic solvent is preferably acetonitrile.

The bases used in process variant ($\beta$) can be strong inorganic or organic bases. Sodium methylate is preferred.

In the process variant ($\beta$) described above, the reaction temperatures can be varied within a certain range. In general, the reaction is carried out at temperatures between 0° C. and 60° C., preferably at room temperature.

The process for the preparation of the oxiranes of the formula (II) in accordance with variant ($\beta$), and the working-up of the reaction product obtained in this synthesis, are carried out according to customary methods [compare Heterocycles 8, 397 (1977)].

The oxiranes of the formula (II) can be further reacted directly, if required without isolation, in the process according to the invention.

Formula (III) gives a general definition of the azoles additionally to be used as starting materials for the process according to the invention. in this formula, X preferably has the meanings which have already been mentioned in the definition of the invention for these substituents. M preferably represents hydrogen, sodium or potassium.

Formula (Ia) gives a general definition of the compounds to be used as starting materials for carrying out a possible oxidation according to the invention. The compounds of the formula (Ia) are substances according to the invention.

The oxidation according to the invention is effected by reaction with customary inorganic or organic oxidising agents. These preferably include organic peracids, such as, for example, peracetic acid, p-nitroperbenzoic acid and m-chloroperbenzoic acid inorganic peracids, such as, for example, periodic acid; and furthermore hydrogen peroxide in glacial acetic acid or methanol, potassium permanganate and chromic acid.

Organic solvents which are inert under the reaction conditions are suitable diluents for the process according to the invention. These preferably include alcohols, such as, for example, ethanol, methoxyethanol or propanol; ketones, such as, for example, butan-2-one nitriles, such as, for example, acetonitrile; esters, such as, for example, ethyl acetate, ethers, such as, for example, dioxane; aromatic hydrocarbons, such as, for example, benzene and toluene; or amides, such as, for example, dimethylformamide.

All customarily usable inorganic and organic bases are suitable bases for the reaction according to the invention. These preferably include alkali metal carbonates, such as, for example, sodium carbonate and potassium carbonate alkali metal hydroxides, such as, for example, sodium hydroxide; alkali metal alcoholates, such as, for example, sodium methylate, sodium ethylate, potassium methylate and potassium ethylate; alkali metal hydrides, such as, for example, sodium hydride and lower tertiary alkylamines, cycloalkylamines and aralkylamines, such as, in particular, triethylamines.

In carrying out the process according to the invention, the reaction temperatures can be varied within a relatively wide range. In general, the reaction is carried out at temperatures between 0° and 200° C., preferably between 60° and 150° C.

In carrying out the process according to the invention, 1 to 2 mols of the azole of the formula (III) and, if appropriate, 1 to 2 mols of a base are preferably employed per mol of the oxirane of the formula (II); the end products are isolated in a generally customary manner.

In carrying out the oxidation according to the invention, the reaction temperatures can be varied within a relatively wide range. In general, the reaction is carried out at between about −50° and 100° C., preferably between −30° and 80° C.

In carrying out the oxidation according to the invention, about 1 to 5 mols of oxidising agent are employed per mol of the compounds according to the invention, of the formula (Ia). When 1 mol of oxidising agent, such as m-chloroperbenzoic acid in methylene chloride or hydrogen peroxide in acetic anhydride, are used at temperatures between −30° and +30° C., the compounds according to the invention, of the formula (I), which have the —SO grouping are preferentially formed. When an excess of oxidising agent and higher temperatures (10° to 80° C.) are used, the compounds according to the invention, of the formula (I), which have the —SO$_2$ grouping are preferentially formed. The oxidation products are isolated in a customary manner.

The acid addition salts of the compounds of the formula (I) can be obtained in a simple manner according to customary salt formation methods for example by dissolving a compound of the formula (I) in a suitable inert solvent and adding the acid, for example hydrochloric acid, and can be isolated in a known manner, for example by filtration, and if appropriate purified by washing with an inert organic solvent.

The compounds of the formula (I) which can be used according to the invention, and their acid addition salts, display antimicrobial actions, in particular powerful antimycotic actions. They possess a very broad antimycotic action spectrum, especially against dermatophytes and blastomyces as well as biphase fungi, for example against varieties of Candida, such as *Candida albicans*, varieties of Epidermophyton, such as *Epidermophyton floccosum*, varieties of Aspergillus, such as *Aspergillus niger* and *Aspergillus fumigatus*, varieties of Trichophyton, such as *Trychophyton mentagrophytes*, varieties of Microsporon, such as *Microsporon felineum* and varieties of Torulopsis, such as *Torulopsis glabrata*. The listing of these microorganisms in no way implies a limitation of the germs which can be combated but is only of illustrative character.

Examples which may be mentioned of fields of indication in medicine are: dermatomycoses and systemic mycoses caused by *Trichophyton mentagrophytes* and other varieties of Trichophyton, varieties of Microsporon, *Epidermophyton floccosum*, blastomyces and biphase fungi as well as moulds.

The present invention includes pharmaceutical formulations which, in addition to non-toxic, inert pharmaceutically suitable excipients, contain one or more active compound according to the invention, or which consist of one or more active compound according to the invention, as well as processes for the preparation of these formulations The present invention also includes pharmaceutical formulations in dosage unit form, for example tablets, dragees, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the compounds listed under (a) to (i).

The tablets dragees capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes creams and gels can contain, in addition to the active compound or compounds, the customary excipients, for example animal and vegetable fats, waxes, paraffins, starches, tragacanth, cellulose derivatives polyethylene glycols, silicones, bentonites, silica, talc and zinc oxide, or mixtures of these substances.

Powders and sprays can contain, in addition to the active compound or compounds, the customary excipients, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, micro-crystalline cellulose, aluminium methahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in medicine, for the treatment of the abovementioned diseases.

The active compounds or the pharmaceutical formulations can be administered locally, orally, parenterally, intraperitoneally and/or rectally, preferably parenterally, and in particular intravenously.

In general, it has proved advantageous in medicine, to administer the active compound or compounds according to the invention in total amounts of about 10 to about 300, preferably 50 to 200, mg/kg of body weight every 24 hours, optionally in the form of several individual administrations, in order to achieve the desired results.

However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, whilst in other cases the abovementioned amount of active compound must be exceeded The particular optimum dosage required and type of administration of the active compounds can easily be determined by anyone skilled in the art on the basis of his expert knowledge.

PREPARATION EXAMPLES

EXAMPLE 1

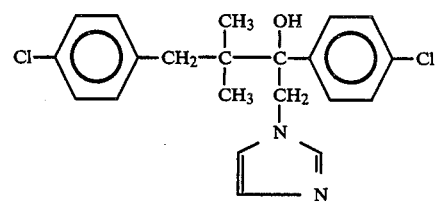

30 g (0.0935 mol) of 2-(4-chlorophenyl)-2-(4-chlorophenyl-tert.-butyl)-oxirane in 40 ml of n-propanol are added dropwise to a solution of 7.7 g (0.108 mol) of imidazolyl-sodium in 60 ml of n-propanol at the reflux temperature. The reaction mixture is stirred under reflux for a further 48 hours and cooled, water is added, and the mixture is extracted with methylene chloride. The organic phase is dried over sodium sulphate and concentrated in vacuo. The oily residue is stirred in diisopropyl ether. The crystalline precipitate formed is filtered off under suction and dried. 12.7 g (35% of theory) of 2,4-bis(4-chlorophenyl)-3,3-dimethyl-1-(imidazol-1-yl)-butan-2-ol of melting point 174° C. are obtained.

Preparation of the starting material

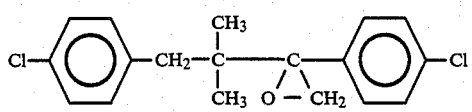

A solution of 59.2 g (0.47 mol) of dimethyl sulphate and 32 g (0.517 mol) of dimethyl sulphide in 270 ml of acetonitrile is stirred for 5 days at room temperature. A solution of 81.5 g (0.2655 mol) of 4-chlorophenyl 4-chlorophenyl-tert.-butyl ketone in 80 ml of acetonitrile is then added dropwise at 20° to 25° C., in the course of approx. 2 hours 28.7 g (0.53 mol) of sodium methylate are added at the same temperature. The total reaction mixture is stirred for 12 hours and thereafter concentrated in vacuo. The residue is stirred overnight with a mixture of 200 ml of ethyl acetate and 150 ml of water. The organic phase is separated off, dried over sodium sulphate and concentrated in vacuo. 72.6 g (85.2% of theory) of crude 2-(4-chlorophenyl)-2-(4-chlorophenyl-tert.-butyl)-oxirane are obtained and this compound is directly reacted further.

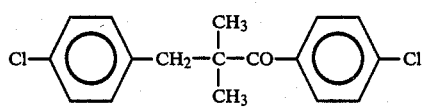

85 g (0.466 mol) of 4-chlorophenyl isopropyl ketone, 31.3 g (0.56 mol) of potassium hydroxide and 5 g of tetrabutylammonium bromide in 120 ml of toluene are heated to the reflux temperature, and a solution of 75 g (0.466 mol) of 4-chlorobenzyl chloride in 60 ml of toluene is added dropwise. The reaction mixture is stirred under reflux for a further 12 hours, cooled, and washed with water, and the organic phase is dried over sodium sulphate and concentrated in vacuo. 81.5 g (60% of theory) of 4-chlorophenyl 4-chlorophenyl-tert.-butyl ketone of refractive index $n_D^{20}=1,5711$ are obtained.

EXAMPLE 2

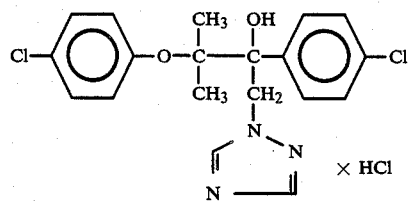

A solution of 30 g (0.093 mol) of 2-(4-chlorophenyl)-2-[2-(p-chlorophenoxy)-prop-2-yl]-oxirane in 40 ml of n-propanol is added dropwise to a solution of 7.6 g (0.107 mol) of 1,2,4-triazolyl-sodium in 60 ml of n-propanol, at room temperature. The reaction mixture is stirred at the reflux temperature for a further 48 hours and is cooled, water is added and the mixture is extracted with methylene chloride. The organic phase is dried over sodium sulphate and concentrated in vacuo. The oily residue is purified by column chromatography. 6.7 g (18.4% of theory) of 3-(4-chlorophenoxy)-2-(4-chlorophenyl)-3-methyl-1-(1,2,4-triazol-1-yl)-butan-2-ol are obtained. This is stirred with 20 ml of saturated hydrogen chloride/ether solution, at room temperature. The precipitate which separates out is filtered off under suction, rinsed with a small amount of ether and dried in vacuo at 40° C. 6.5 g (89% of theory, relative to base employed) of 3-(4-chlorophenoxy)-2-(4-chlorophenyl)-3-methyl-1-(1,2,4-triazol-1-yl)-butan-2-ol hydrochloride of melting point 135° C. are obtained.

Preparation of the starting material

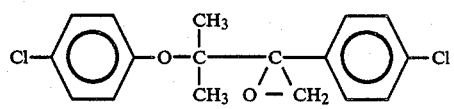

A solution of 59.2 g (0.47 mol) of dimethyl sulphate and 32 g (0.517 mol) of dimethyl sulphide in 270 ml of acetonitrile is stirred at room temperature for 5 days. A solution of 87 g of 4-chlorophenyl 2-(p-chlorophenoxy)-prop-2-yl ketone in 80 ml of acetonitrile is then added dropwise at 20° to 25° C., in the course of approx. 2 hours. 28.7 g (0.53 mol) of sodium methylate are introduced at the same temperature, and the mixture is stirred for a further 12 hours and then concentrated. The residue is stirred overnight with a mixture of 200 ml of ethyl acetate and 150 ml of water. The organic phase is separated off, dried over sodium sulphate and concentrated in vacuo. 49 g (76% of theory) of crude 2-(4 chlorophenyl)-2-[2-(p-chlorophenoxy)-prop-2-yl]-oxirane are obtained, and this compound is directly reacted further.

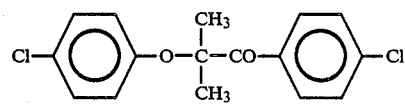

52 g (0.3982 mol) of p-chlorophenol and 55 g (0.3982 mol) of potassium carbonate in 400 ml of toluene are heated under reflux for 2 hours in a water separator. The mixture is cooled to 40° C., and a solution of 2-bromo-prop-2-yl 4-chlorophenyl ketone in 170 ml of toluene is added dropwise. This reaction mixture is stirred for a further 5 hours at 100° C. and then cooled, water is added and the organic phase is separated off. This is washed with dilute sodium hydroxide solution and water, dried over sodium sulphate and concentrated. 87 g (85% of theory) of crude 4-chlorophenyl 2-(p-chlorophenoxy)-prop-2-yl ketone are obtained, and this compound is directly reacted further.

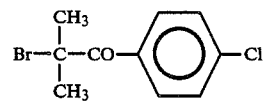

1 ml of hydrogen bromide/glacial acetic acid is added to 65.5 g (0.36 mol) of 4-chlorophenyl isopropyl ketone in 200 ml of chloroform, and 57.5 g (0.36 mol) of bromine are then added dropwise at 30° C. The mixture is stirred for a further 30 minutes at room temperature, and thereafter concentrated in vacuo. 86.6 g (92% of theory) of crude 2-bromo-prop-2-yl 4-chlorophenyl ketone are obtained, and this compound is directly reacted further.

The following compounds of the formula

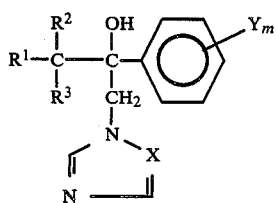

(I)

are obtained in a corresponding manner and in accordance with the process as exemplified according to the invention:

| Example No. | R¹ | R² | R³ | X | $Y_m$ | Melting point - (°C.) |
|---|---|---|---|---|---|---|
| 3 | 4-Cl-C₆H₄- | CH₃ | CH₃ | CH | 4-Cl | 138 |
| 4 | 4-Cl-C₆H₄-CH₂- | CH₃ | CH₃ | N | 4-Cl | 137 |
| 5 | 4-Cl-C₆H₄- | CH₃ | CH₃ | N | 4-Cl | 109 |
| 6 | C₆H₅-CH₂- | CH₃ | CH₃ | N | 4-F | 120 |
| 7 | C₆H₅-CH₂- | CH₃ | CH₃ | CH | 4-F | 118–120 |
| 8 | 4-Cl-C₆H₄-CH₂- | CH₃ | CH₃ | CH | 4-F | 165–167 |
| 9 | 4-Cl-C₆H₄-CH₂- | CH₃ | CH₃ | N | 4-F | 124 |
| 10 | 4-F-C₆H₄-CH₂- | CH₃ | CH₃ | CH | 4-Cl | 126 |
| 11 | 4-F-C₆H₄-CH₂- | CH₃ | CH₃ | N | 4-Cl | 112 |
| 12 | 2,3-Cl₂-C₆H₃-CH₂- | CH₃ | CH₃ | CH | 4-F | 93 |
| 13 | 4-F-C₆H₄-CH₂- | CH₃ | CH₃ | CH | — | 164–65 |

| Example No. | R¹ | R² | R³ | X | Y_m | Melting point - (°C.) |
|---|---|---|---|---|---|---|
| 14 |  4-Cl-C6H4-S- | CH₃ | CH₃ | N | 4-Cl | 74–76 |
| 15 | 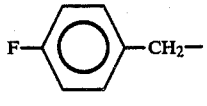 4-F-C6H4-CH2- | CH₃ | CH₃ | N | — | 102–04 |
| 16 |  4-Cl-C6H4-S- | CH₃ | CH₃ | CH | 4-Cl | 94 |
| 17 | 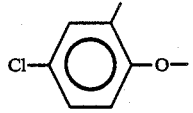 2,4-diCl-C6H3-O- | CH₃ | CH₃ | CH | 4-Cl | 80–82 |
| 18 | 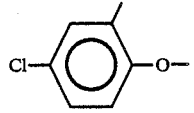 2,4-diCl-C6H3-O- | CH₃ | CH₃ | N | 4-Cl | 96–98 |
| 19 | 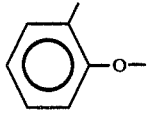 2-Cl-C6H4-O- | CH₃ | CH₃ | N | 4-Cl | 114–16 |
| 20 | 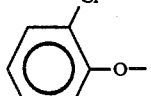 2-Cl-C6H4-O- | CH₃ | CH₃ | CH | 4-Cl | 194 |
| 21 | 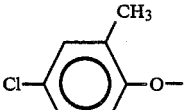 4-Cl-2-CH3-C6H3-O- | CH₃ | CH₃ | N | 4-Cl | 117 |
| 22 | 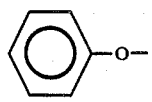 C6H5-O- | CH₃ | CH₃ | N | 4-Cl | 82 |
| 23 | 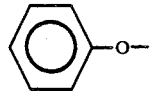 C6H5-O- | CH₃ | CH₃ | CH | 4-Cl | 188 |
| 24 | 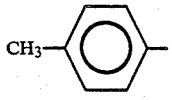 4-CH3-C6H4- | CH₃ | CH₃ | N | 4-Cl | 62 |
| 25 | 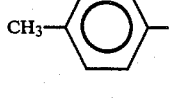 4-CH3-C6H4- | CH₃ | CH₃ | CH | 4-Cl | 106 |

-continued

| Example No. | R¹ | R² | R³ | X | $Y_m$ | Melting point - (°C.) |
|---|---|---|---|---|---|---|
| 26 | 4-Cl-C₆H₄-O-CH₂- | C₂H₅ | CH₃ | N | 4-Cl | 104–106 |
| 27 | 4-Cl-C₆H₄-O- | C₂H₅ | CH₃ | N | 4-Cl | 182–84 (× HCl) |
| 28 | 4-F-C₆H₄-CH₂- | CH₃ | CH₃ | N | 4-F | 118 |
| 29 | 4-Cl-C₆H₄-O- | CH₃ | CH₃ | N | 4-F | 82 |
| 30 | 4-F-C₆H₄-O- | CH₃ | CH₃ | N | 4-F | 78 |
| 31 | 4-Cl-C₆H₄-O- | CH₃ | CH₃ | CH | 4-F | 154 |
| 32 | 4-F-C₆H₄-O- | CH₃ | CH₃ | CH | 4-F | 178 |
| 33 | 4-F-C₆H₄-CH₂- | CH₃ | CH₃ | CH | 4-F | 50 |
| 34 | 4-F-C₆H₄-O- | C₂H₅ | CH₃ | N | 4-F | 114 |
| 35 | 4-Cl-C₆H₄-O- | C₂H₅ | CH₃ | N | 4-F | 66 |
| 36 | 2-F-C₆H₄-O- | CH₃ | CH₃ | N | 4-F | 120 |
| 37 | 2-Cl-C₆H₄-O- | CH₃ | CH₃ | N | 4-F | 147 |

USE EXAMPLES

The compounds indicated below are employed as comparative substances in the examples which follow:

(A)

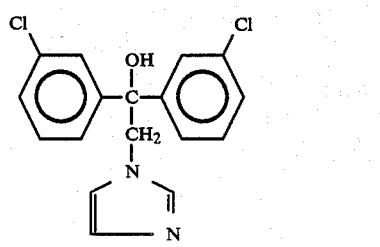

(B)

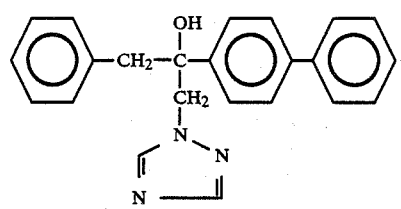

(C)

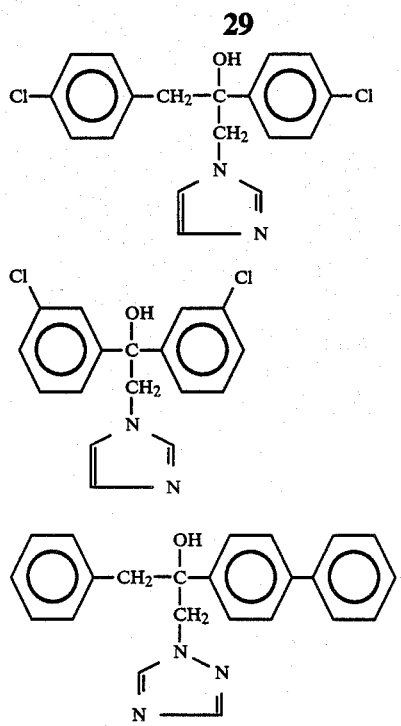

EXAMPLE A

Antimycotic in vitro activity

Description of the experiment

The in vitro tests were carried out in series dilution test with germ inocula of an average of $5\times10^4$ germs/ml of substrate. The nutrient medium was (a) for dermatophytes and moulds: Sabourand's milieu d'epreuve and (b) for yeasts: meat extract/glucose broth.

The incubation temperature was 20° C. and the duration of incubation was 24 to 96 hours in the case of yeasts, and 96 hours in the case of dermatophytes and moulds.

In this test, the compounds of Examples 1, 2, 3, 4, 5, 6, 8, 9, 10, 11, 12, 14, 15, 16, 18, 19, 20, 21, 22, 23, 25, 26, 28, 29 and 35 in particular, showed a better antimycotic action than the compounds (A), (B) and (C) which are known from the prior art.

TABLE A

| | Antimycotic in vivo activity | | | |
|---|---|---|---|---|
| | MIC values in ?/ml of nutrient medium for | | | |
| Active compound | Tricho-phyton mentagr. | Micro-sporum canis | Candida albi-cans | Torul-opsis glab-rata |
| (A) (known) | 32 | 64 | 16 | 32 |
| (B) (known) | 16 | 32 | 16 | 16 |
| (C) (known) | <1 | 16 | >64 | — |
| Compounds according to preparation Example | | | | |
| 1 | ≦1 | 8 | 4 | ≦1 |
| 2 | ≦1 | 16 | 16 | 8 |
| 3 | 4 | 16 | 4 | 16 |
| 4 | ≦1 | 16 | ≦1 | 4 |
| 5 | ≦1 | ≦1 | 16 | 4 |
| 6 | ≦1 | 4 | 4 | 16 |
| 8 | ≦1 | 8 | 8 | 16 |
| 9 | ≦1 | 8 | 2 | 8 |
| 10 | ≦1 | 8 | ≦1 | ≦1 |
| 11 | ≦1 | 8 | 8 | 4 |

TABLE A-continued

| | Antimycotic in vivo activity | | | |
|---|---|---|---|---|
| | MIC values in ?/ml of nutrient medium for | | | |
| Active compound | Tricho-phyton mentagr. | Micro-sporum canis | Candida albi-cans | Torul-opsis glab-rata |
| 12 | 4 | 16 | 4 | 4 |
| 14 | ≦1 | 8 | 4 | 4 |
| 15 | 2 | 8 | 8 | 32 |
| 16 | ≦1 | 16 | ≦1 | ≦1 |
| 18 | ≦1 | 8 | 8 | 8 |
| 19 | ≦1 | 8 | ≦1 | 16 |
| 20 | ≦1 | 8 | 8 | ≦1 |
| 21 | ≦1 | 8 | 8 | 4 |
| 22 | ≦1 | 4 | 16 | 32 |
| 23 | 2 | 16 | 8 | 16 |
| 25 | ≦1 | 16 | ≦1 | 2 |
| 26 | ≦1 | ≦1 | 4 | 4 |
| 28 | ≦1 | 16 | 8 | 16 |
| 29 | ≦1 | 8 | 8 | 16 |
| 35 | ≦1 | 16 | 8 | 8 |

EXAMPLE B

Antimycotic in vivo activity (oral) in candidosis of mice

Description of the experiment

Mice of the SPF-CF type were infected intravenously with $1-2\times10^6$ logarithmically growing Candida cells, which were suspended in physiological sodium chloride solution. The animals were treated orally one hour before and seven hours after the infection, with, in each case, 25-100 mg/kg of body weight of the formulations.

Result

Untreated animals died 3 to 6 days after infection. The survival rate on the 6th day after infection was about 5% in the case of untreated control animals. In this test, for example, the compounds 1, 4, 8, 9, 11, 17, 18, 26, 27, 28, 29, 30, 31, 32, 33, 34 and 35 according to the invention exhibited a better action than the compounds (A), (B) and (C) which are known from the prior art.

| Explanation of symbols | |
|---|---|
| +++++ = very good action | = 90% survival on the 6th day after infection |
| ++++ = good action | = 80% survival on the 6th day after infection |
| +++ = action | = 60% survival on the 6th day after infection |
| ++ = slight action | = 40% survival on the 6th day after infection |
| + = trace of an action | = |
| n.a. = no action | |

TABLE 3

| Antimycotic in vivo activity (oral) in candidosis of mice | |
|---|---|
| Active compound | Action |
| (A) (known) | + |
| (B) (known) | n.a. |
| (C) (known) | n.a. |
| Compounds according to Preparation Example | |
| 1 | +++ |
| 4 | +++++ |
| 8 | ++++ |
| 9 | +++++ |

TABLE 3-continued

| Antimycotic in vivo activity (oral) in candidosis of mice | |
|---|---|
| Active compound | Action |
| 11 | +++++ |
| 17 | +++ |
| 18 | +++++ |
| 26 | ++++ |
| 27 | ++++ |
| 28 | ++++ |
| 29 | ++++ |
| 30 | ++++ |
| 31 | +++ |
| 32 | ++++ |
| 33 | +++ |
| 34 | +++ |
| 35 | ++++ |

EXAMPLE C/FORMULATIONS

| (1.) Solution | |
|---|---|
| Active compound according to formula (I) | 10 g |
| Alcohol, pure (96% strength) | 300 g |
| Isopropyl myristate | 526 g |
| | 836 g |
| (2.) Cream: | |
| Active compound according to formula (I) | 10 g |
| Arlacel 60 | 20 g |
| (Sorbitane monostearate) | |
| Tween 60 | 15 g |
| (Polyoxyethylene(2)-sorbitane monostearate) | |
| Spermaceti, synthetic | 30 g |
| (Mixture of esters of saturated $C_{14}$—$C_{18}$ fatty acids and $C_{14}$—$C_{18}$ fatty alcohols) | |
| Lanette O | 100 g |
| (Mixture of cetyl alcohol and stearyl alcohol) | |
| Entanol G | 135 g |
| (2-Octyl-dodecanol) | |
| Benzyl alcohol | 10 g |
| Water, demineralised | 680 g |
| | 1000 g |

We claim:

1. A substituted hydroxyalkyl-azole of the formula

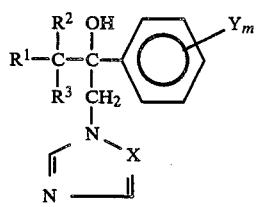

in which
R$^1$ represents phenyl or —O—phenyl, each of which is monosubstituted to disubstituted by identical or different substituents, the phenyl substituents having the meaning of Y;
R$^2$ represents straight-chain or branched alkyl having 1 to 4 carbon atoms;
R$^3$ represents straight-chain or branched alkyl having 1 to to 4 carbon atoms;
X represents a nitrogen atom or the CH group;
Y represents halogen or alkyl having 1 to 4 carbon atoms, alkoxy and alkylthio, each having 1 to 4 carbon atoms, halogenoalkyl and halogenoalkoxy and halogenoalkylthio, each having 1 to 2 carbon atoms and 1 to 5 identical or different halogen atoms, and represents phenyl, phenoxy, phenylalkyl and phenylalkoxy which have 1 to 2 carbon atoms in the alkyl part or in the alkoxy part, and each of which are optionally substituted by halogen and alkyl having 1 to 2 carbon atoms and m represents the number 0, 1, 2 or 3.

2. A substituted hydroxyalkyl-azole of claim 1 wherein the halogenoalkyl, halogenoalkoxy and halogenoalkylthio moieties have, as halogen atoms, fluorine or chlorine atoms.

3. A substituted hydroxyalkyl-azole according to claim 1, in which
R$^1$ represents phenyl or —O—phenyl, each of which is monosubstituted to disubstituted by identical or different substituents, the phenyl substituents have the meaning of Y,
R$^2$ represents methyl or ethyl,
R$^3$ represents methyl or ethyl,
X represents a nitrogen atom or the CH group
Y represents fluorine, chlorine, bromine, methyl, isopropyl, tert.-butyl, cyclohexyl, methoxy, methylthio, trifluoromethyl, trifluoromethoxy and trifluoromethylthio, and represents phenoxy, benzyl, benzyloxy or phenyl which is optionally substituted by fluorine, chlorine or methyl; and m represents the numbers 0, 1, 2 or 3.

4. A substituted hydroxyalkyl-azole of claim 1 which is 2,4-Bis(4-chlorophenyl)-3,3-dimethyl-1-(imidazol-1-yl)-butan-2-ol.

5. A substituted hydroxyalkyl-azole of claim 1 which is 3-(4-Chlorophenoxy)-2-(4-chlorophenyl)-3-methyl-1-(1,2,4-triazol-1-yl)-butan-2-ol.

6. A pharmaceutical composition comprising an antimycotically effective amount of a compound of claim 1 together with an inert pharmaceutical excipient.

7. A pharmaceutical composition of claim 6 wherein the active compound is 2,4-Bis(4-chlorophenyl)-3,3-dimethyl-1-(imidazol-1-yl)-butan-2-ol.

8. A pharmaceutical composition of claim 6 wherein the active compound is 3-(4-Chlorophenoxy)-2-(4-chlorophenyl)-3-methyl-1-(1,2,4-triazol-1-yl)-butan-2-ol.

9. A pharmaceutical composition of claim 6 in the form of a sterile or physiologically isotonic aqueous solution.

10. A medicament in dosage unit form comprising an antimycotically effective amount of a compound of claim 1 either alone or in admixture with an inert pharmaceutical excipient.

11. A medicament of claim 10 in the form of tablets, pills, dragees, capsules, ampoules or suppositories.

12. A method of combatting mycoses in warm blooded animals which comprises administering to said animal an antimycotically effective amount of a compound of claim 1 either alone or in admixture with an inert excipient or in the form of a medicament.

13. A method of claim 12 wherein the active compound is administered orally.

14. A method of claim 12 wherein the active compound is administered parenterally.

* * * * *